United States Patent
Clara et al.

(10) Patent No.: US 10,417,856 B2
(45) Date of Patent: Sep. 17, 2019

(54) DEVICE AND METHOD FOR VERIFYING FEATURE SUBSTANCES

(71) Applicant: GIESECKE & DEVRIENT GMBH, München (DE)

(72) Inventors: Martin Clara, München (DE); Thomas Giering, Kirchseeon (DE); Johann Kecht, München (DE); Wolfgang Rauscher, Parkstetten (DE); Martin Stark, München (DE); Thomas Happ, München (DE)

(73) Assignee: GIESECKE & DEVRIENT GMBH, München (DE)

( * ) Notice: Subject to any disclaimer, the term of this patent is extended or adjusted under 35 U.S.C. 154(b) by 74 days.

(21) Appl. No.: 15/536,917

(22) PCT Filed: Dec. 16, 2015

(86) PCT No.: PCT/EP2015/002537
§ 371 (c)(1),
(2) Date: Jun. 16, 2017

(87) PCT Pub. No.: WO2016/096133
PCT Pub. Date: Jun. 23, 2016

(65) Prior Publication Data
US 2017/0358163 A1    Dec. 14, 2017

(30) Foreign Application Priority Data

Dec. 16, 2014    (DE) .................. 10 2014 018 726

(51) Int. Cl.
*G07D 7/1205*    (2016.01)
*G01N 21/65*    (2006.01)

(52) U.S. Cl.
CPC .......... *G07D 7/1205* (2017.05); *G01N 21/65* (2013.01); *G01N 21/658* (2013.01)

(58) Field of Classification Search
CPC ............................. G07D 7/1205; G07D 7/122
See application file for complete search history.

(56) References Cited

U.S. PATENT DOCUMENTS

| 6,061,121 A | 5/2000 | Holl et al. |
|---|---|---|
| 7,737,417 B2 | 6/2010 | Giering et al. |

(Continued)

FOREIGN PATENT DOCUMENTS

| DE | 102004035494 A1 | 2/2006 |
|---|---|---|
| EP | 0806460 B1 | 7/2002 |

(Continued)

OTHER PUBLICATIONS

International Search Report From PCT Application No. PCT/EP2015/002537, dated Mar. 3, 2016.

(Continued)

*Primary Examiner* — Hina F Ayub
*Assistant Examiner* — Amanda Merlino
(74) *Attorney, Agent, or Firm* — Workman Nydegger

(57) ABSTRACT

The invention relates to an apparatus and a method for checking value documents marked with feature substances, and to the corresponding feature substances. The feature substances are detected on the basis of Raman or SERS spectroscopy also at high transport speeds with a spatial resolution in the low millimeter region or better and reliably identified.

18 Claims, 5 Drawing Sheets

(56) References Cited

U.S. PATENT DOCUMENTS

| | | | |
|---|---|---|---|
| 8,107,712 B2* | 1/2012 | Holl | G07D 7/121 |
| | | | 356/71 |
| 2008/0135780 A1* | 6/2008 | Giering | G07D 7/121 |
| | | | 250/459.1 |
| 2009/0141961 A1 | 6/2009 | Smith et al. | |
| 2009/0174879 A1* | 7/2009 | Bloss | G07D 7/1205 |
| | | | 356/71 |
| 2011/0049239 A1* | 3/2011 | Kukushkin | G01N 21/658 |
| | | | 235/454 |
| 2011/0188054 A1* | 8/2011 | Petronius | B23P 11/00 |
| | | | 356/610 |

FOREIGN PATENT DOCUMENTS

| | | |
|---|---|---|
| EP | 1385637 B1 | 8/2011 |
| WO | 9111492 A1 | 8/1991 |
| WO | 96396021 A1 | 11/1996 |
| WO | 2006010537 A1 | 2/2006 |
| WO | 2007146753 A2 | 12/2007 |
| WO | 2012030988 A1 | 3/2012 |
| WO | 2014022330 A2 | 2/2014 |

OTHER PUBLICATIONS

He et al., "Baseline Correction for Raman Spectra Using an Improved Asymmetric Least Squares Method", Analytical Methods vol. 6, 2014, pp. 4402-4407.

Zhang et al., "An Intelligent Background-Correction Algorithm for Highly Fluorescent Samples in Raman Spectroscopy", Journal of Raman Spectroscopy vol. 41, 2010, pp. 659-669.

\* cited by examiner

DEVICE AND METHOD FOR VERIFYING FEATURE SUBSTANCES

BACKGROUND

The invention relates to an apparatus and a method for checking value documents marked with feature substances, and to the corresponding feature substances.

For safeguarding objects or in particular value documents such as bank notes, checks, passports, cards, etc. against forgeries, for quite some time here have been applied or incorporated feature substances as security features, whose presence can be proven by measuring their characteristic properties and employed for the authentication of the value document. A special class among these are machine-readable security features which, for example, are based on magnetic, photo-luminescent, electric-luminescent, optical absorption or further spectroscopic properties of the feature substances. In most cases, these cannot be recognized with the naked eye, but for authentication are detected and checked with a sensor specialized therein. In particular in the field of checking authenticity and state of bank notes by machine, in bank note processing machines these are guided past a series of sensors with high speeds, e.g. more than 11 m/s, and are automatically checked, evaluated and sorted.

In doing so, it is desirable that not only one measuring point per value document is obtained, but the total value document is scanned in spatially resolved manner. This increases the security of the authenticity check, on the one hand, because with an appropriate spatial extent of the security marking on the value document, also composite forgeries can then be recognized. Such forgeries are composed of pieces of different segments or portions of authentic value documents and other forged segments.

Furthermore, with a spatially resolved detection of a spatially locally attached security marking not only its general presence can be proven, but also its correct positioning on the document can be checked.

With a spatially resolved detection there can be additionally read out, due to the recognition of a security marking spatially attached e.g. in the form of a bar code, additional information about e.g. kind, series, value etc. of the value document.

In the literature there can be found several descriptions for marking value documents with Raman-active matter or in particular surface-enhanced Raman-scattering (SERS) active matter as well as their detection for securing the authenticity.

For example, WO 91/119492 A1 describes the safeguarding of value documents with a printing ink with fine-grained Raman-active components. These are proven upon irradiation with laser light of only few mW with the help of their characteristic Raman signal at powers to be detected in the pW region.

In EP 0806460 B1, the marking and safeguarding of value documents with a security ink containing SERS or surface-enhanced resonant Raman-scattering (SERRS) active matter is described. In so doing, the relatively weak Raman signals of the marker matters are often drastically amplified, by e.g. 6 orders of magnitude, by surface plasmonic effects occurring on the surface of metallic nanoparticles (SERS). In the case of the resonant Raman scattering the excitation wavelength is put spectrally in the vicinity of an electronic transition of the marker substance to be proven, which due to the resulting resonance entails a further significant amplification of the Raman signal. For the proof there are used classical instruments for stationary Raman spectroscopy in a microscope construction. Although these offer in principle an excellent spatial resolution, they have the serious disadvantage that typical measurement durations in the range of seconds up to several minutes are very long and hence are unsuitable for fast moved substrates.

EP 1385637 B1 also describes machine-readable security markings for value documents having a plurality of suitable marker substances or Raman-active molecules. For the authenticity proof there is employed, besides conventional commercial Raman spectrometers, a special portable Raman sensor with excitation in the infrared region and a CCD detector with 2048 pixels of linear resolution. Recording durations with integration times of 5 s to 60 s are achieved.

In WO 2014/022330 A2 SERS nanomarkers for securing the authenticity and the proof thereof with a confocal Raman microscope or a portable Raman spectrometer are described. In both cases the measurement duration of 5 s or 20 s is far too slow for being suitable for fast moved samples.

In WO 2007/146753 A2 there is described an in principle universally employable high speed Raman spectrometer which with an optomechanical rotary time-division multiplexer directs the individual wavelength channels respectively defined by a tailored bandpass spectral filter in a time shifted manner to one single very quickly readable detector. By this approach spectra within 1-100 ms can be obtained. This, however, offers no sufficient spatial resolution for fast moved samples, particularly because the here obtained spectra are spatially/spectrally smeared. Due to the staggered-in-time detection of the different spectral channels the intensity information of the different spectral channels does not come from the same place, but depending on the detection time of the specific channel from a place further away on the sample moved further.

In WO 2012/030988 A1 there is described an inline spectral sensor for SERS- or Raman-marked moved objects. This includes a fiber-coupled measurement head with connection to the light source as well as to the spectrometer which is equipped with a CCD-based detector. The spectral resolution here is to be between 0.01 nm and 5000 nm. A measuring time for recording a spectrum at an SERS-marked document of 5 ms at a speed of 10 m/s is achieved, which—if immediately repeatable—corresponds to a spatial resolution of at best 5 cm. This is not sufficient for an authenticity determination with position check of the marking substance on the value document or for a recognition of bar codes.

For the machine check of the authenticity of moved luminescent value documents, such as for example bank notes, there are further known sensors, e.g. from WO 2006/010537 A1, which check the luminescence properties of marking substances attached thereto spectroscopically. However, these are not suitable for measuring Raman or SERS signals. The Raman signals occur in a spectral region which with a typical shift of possibly only few 1-100 $cm^{-1}$ is very near to the excitation laser wavelength and—in contrast to luminescent signals—cannot be separated in a time-resolved manner via an afterglow. Moreover, the intensity of the Raman lines is very small in comparison to the Rayleigh line of the elastically scattered excitation light. Therefore, the existing luminescence sensors are not suitable for the proof of Raman markers, because here the rather weak Raman signals are completely over-irradiated by the Rayleigh-scattered excitation light during the excitation.

Furthermore, imaging and thus spatially resolving sensors for the machine check of moved bank notes are known, for example, from WO 96/36021 A1. These achieve, by recording the light reflected at the bank note via a filtering and recording with line CCD cameras, a spatial resolution smaller than 0.5 mm at speeds higher than 5 m/s. Such cameras, however, are not suitable for the secure identification of Raman-spectroscopy signals, because, firstly, the illumination is unsuitable for generating useful Raman signals, secondly, the necessary spectral resolution with regard to selectivity as well as number of channels is far from being achievable, and, thirdly, the necessary filtering of the intensive excitation light with a suppression by many orders of magnitude is not representable in such an image sensor geometry.

Summing up, the safeguarding of value documents with Raman or SERS marking substances as well as their basic proof by stationary Raman spectroscopy or also by Raman spectroscopy carried out with moved value documents is known. However, there exist no sensors which are able to render the specific proof of a Raman or SERS marker over the document at least along a track in a spatially resolved manner also at transport speeds usual in bank note processing machines of up to 11 m/s or more.

SUMMARY

Starting out from this, the object to be achieved of the present invention is to provide an apparatus and a method for checking value documents, which can detect and reliably identify security features on a Raman or SERS spectroscopic basis also at high transport speeds, e.g. more than 11 m/s, with a spatial resolution in the low millimeter region or better.

Described is a Raman sensor with a drastically increased speed of readout at an at the same time good signal/noise ratio, which achieves the object of the invention as follows. Sensor for the machine check of moved value documents having at least one Raman or SERS or SERRS security feature, wherein, for checking, the sensor is configured to illuminate the value document with excitation light from a laser source and to disperse the resulting Raman light of the security features in a spectrometer and to capture it with spectral resolution with a detector having several spectral channels, whereby the light from the same areal region of the value document collected in the spectral channels is captured synchronously by the detector and measurement signals corresponding to the spectral channels are formed.

The sensor according to the invention is designed to achieve a spatial resolution of less than 12 mm, preferably less than 4 mm, particularly preferably less than 2 mm. As high transport speeds, e.g. 12 m/s or more, may occur for the value documents, in the case of a spatial resolution of 2 mm, in the worst case a time of only approx. 160 μs is available for the measurement of the total spectrum. The design of the sensor is adjusted accordingly to bring as much light as possible onto the detector, on the one hand, so as to achieve a signal/noise ratio as good as possible even with very short integration times. On the other hand, the detector elements which detect the spectrally resolved light must be sufficiently fast and in particular readable synchronously to avoid a spatial/spectral smearing of the spectra caused by the further movement of the bank note during the readout time.

In the solution according to the invention the number of the spectral channels is reduced compared to the Raman spectroscopy devices with 1000-4000 channels which are hitherto known and usual in laboratories or as hand devices. These, however, are preferably completely read out in parallel, thereby actually enabling the high speed of readout essential for a good spatial resolution in the transport direction. By an evaluation of the obtained signals with analysis methods according to the invention a reliable identification of the Raman- or SERS-active feature substances or the recognition of the authenticity connected therewith is surprisingly possible in spite of the reduced resolution.

The sensor according to the invention further has a special optical design of the spectrometer with which a reliable suppression of the Rayleigh-scattered light is possible. In one embodiment, another detector is attached in the sensor in addition to the detector for the Raman light, which measures the spectral location and intensity of the excitation laser light.

The sensor apparatuses according to the invention can be employed in all kinds of apparatuses in which optical radiation, in particular Raman radiation is checked. Although not limited thereto, in the following there will be described on the basis of Figures as a preferred variant the check of bank notes in bank note processing apparatuses which, for example, may serve for counting and/or sorting and/or depositing and/or dispensing bank notes.

Additionally, the invention comprises a method for the machine check of value documents having at least one Raman or SERS or SERRS security feature by means of a sensor, wherein during the check the value document is moved relative to the sensor at high speed, for checking, the value document is illuminated with excitation light from a laser source, the resulting Raman light of the security features is dispersed in a spectrometer and is captured with spectral resolution with a detector having several spectral channels, wherein from the spectral channels there are formed respective measurement signals, wherein the light from the same areal region of the value document collected in the spectral channels is captured synchronously by the detector and spatially resolved measurement signals are formed by repeated measurement.

BRIEF DESCRIPTION OF THE DRAWINGS

Furthermore, the invention comprises a coding system for distinguishing value documents with the sensor according to the invention, whereby the value documents are marked with feature substances or mixtures of feature substances which comprise marker molecules which have strong Raman signals in one or several spectral regions with a respective spectral distance of more than 50 $cm^{-1}$, preferably more than 100 $cm^{-1}$, in particular more than 200 $cm^{-1}$.

There is shown.

DETAILED DESCRIPTION OF VARIOUS EMBODIMENTS

Figure 1:
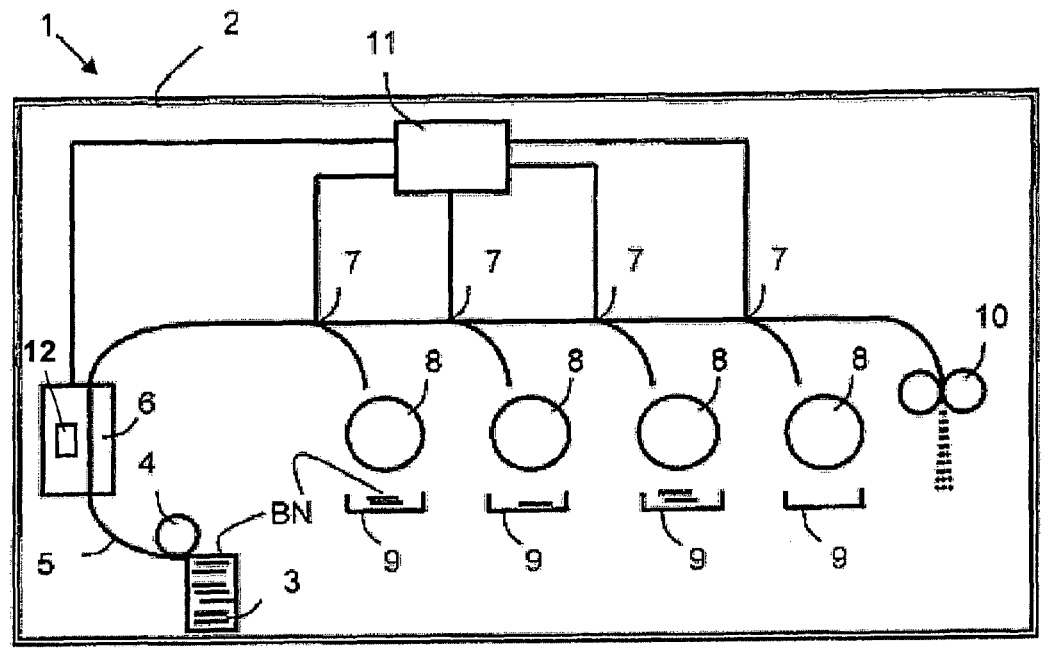
FIG. 1 a bank note sorting apparatus having a Raman sensor.
Figure 2:
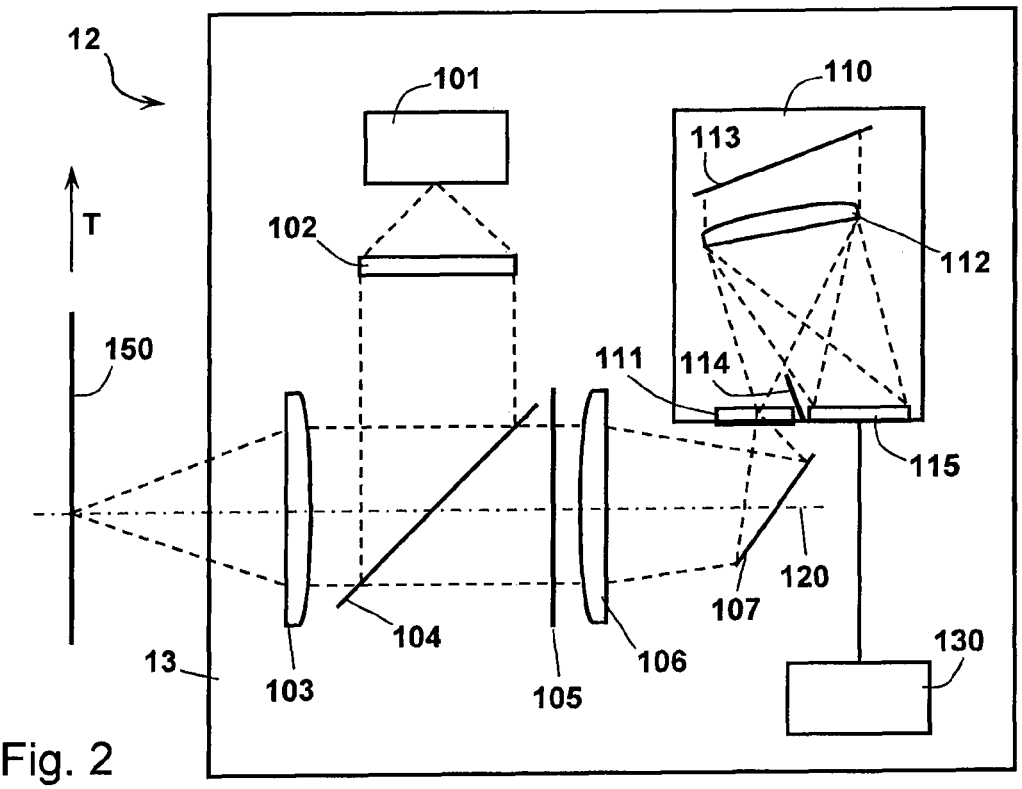
FIG. 2 illustrates in a schematic cross-sectional view the construction and the arrangement of the optical components of a Raman sensor with a particularly compact configuration according to an embodiment example of the present invention, FIG. 3A, B illustrate respectively in a schematic view a partial region of alternative embodiments of the Raman sensor, FIG. 4 a schematic representation for reading out the intensity data from a detector of the Raman sensor, FIG. 5A, B illustrate in a schematic top view (5A) and a cross-sectional view (5B) the construction of an embodiment of an entrance slit module of the Raman sensor with integrated filtering of the light.

In FIG. 1 there is shown by way of example such a bank note sorting apparatus 1. The bank note sorting apparatus 1 here has an input pocket 3 in a housing 2 for bank notes BN into which bank notes BN to be processed are inserted either manually from outside or to which bank-note bundles can be fed automatically or, where applicable, after a preceding debanding. The bank notes BN inserted into the input pocket 3 are drawn off singly from the stack by a singler 4 and transported through a sensor device 6 by means of a transport device 5. The sensor device 6 here may have one or several sensor modules integrated in a joint housing or attached in separate housings. The sensor modules may serve for e.g. checking the authenticity and/or the state and/or the nominal value of the checked bank notes BN. After running through the sensor device 6 the checked bank notes BN are then sorted in dependence on the check results of the sensor device 6 and given sorting criteria and output via gates 7 and associated spiral slot stackers 8 into output pockets 9 from which they can be either removed manually or carried off automatically, where applicable after a preceding banding or packaging. A shredder can also be provided for destroying bank notes BN classified as authentic and no longer fit for circulation. The control of the bank note sorting apparatus 1 is effected by means of a computer-aided control unit 11. As mentioned above, the sensor device 6 may have different sensor modules. The sensor device 6 is characterized in particular by a sensor module 12 (FIG. 2) for checking Raman-scattered excitation light, to be referred to hereinafter for short as Raman sensor 12.

The Raman sensor 12 in particular has in one joint housing 13 a laser source 101 for the excitation of Raman scatter radiation, optical elements such as lenses 102, 103, 106 and filters 105 as well as a spectrometer 110 which has at least one detector 115 for the spectrally decomposed capture of the Raman-scattered light. For coupling out the excitation radiation and for coupling in the scattered light, the housing 13 has an opening which can optionally be closed with a suitable window having high transmission in the relevant spectral region. The window, optionally, has further one or two antireflection coating(s). In one embodiment, the window may also have the form of a non-planar surface in the form of a light-refractive lens. The inner walls of the housing are preferably dyed black, this referring to a low reflectivity in the entire relevant spectral region, in particular including the NIR region. Bank notes to be checked are transported past the Raman sensor 12 in the transport direction T.

In one embodiment, directly opposite of the Raman sensor 12 there is mounted a mechanical stop which limits or stabilizes the location of the moved bank notes relative to the focal position of the sensor. In this way, the flutter motions of the bank notes often occurring at high speeds of e.g. 10 m/s and more and the variations of the focal position occurring in this connection can be avoided. This increases the reliability and accuracy of the Raman measurement.

In an illumination unit the narrow-band light of the laser source 101, which preferably comprises a semiconductor laser, is focussed onto the value document to be checked. Preferably, one or several semiconductor lasers with frequency-selective structures are employed here, which generate a narrow-band, preferably mono-mode emission and stabilize the emission wavelength. The frequency-selective structures may have, for example, gratings with distributed feedback (DFB) or mirrors with distributed feedback (distributed Bragg reflector, DBR) or accordingly short Fabry-Perot resonators as they are used, for example, in vertical cavity surface emitting lasers (VCSEL). As the maximum output power thereof is limited typically to the region of some mW, preferably an array of several VCSELs is used for generating the illumination radiation. The laser light source of the sensor is coupled to a suitable heat sink and preferably actively temperature-stabilized through a Peltier element. In one embodiment the laser temperature is actively monitored by one or several temperature sensing devices to obtain a measure for the output wavelength of the excitation radiation and to use it, where applicable, for the evaluation or correction of the recorded spectra. Optionally, these temperature values are also used for actively regulating the laser temperature. This is necessary in order to stabilize the laser power, on the one hand, and to stabilize the excitation wavelength, on the other hand, because the laser wavelength of DFB lasers or VCSELs, also in the most favourable case of a stable mono-mode operation shifts with approx. 0.06 nm/K. In order for the excitation wavelength to vary less than ±0.5 nm, the temperature of the laser chip must be constantly held at better than ±8 K.

The laser wavelength is selected in dependence on the SERS or Raman feature to be detected. Since in the Raman spectroscopy the frequency of the examination light has no influence on the relative spectral location of the Raman lines, the excitation wavelength is in principle freely selectable (e.g. intensive laser lines etc.). If the excitation wavelength is selected such that an electronic transition is excited, it comes to an amplification effect of particular Raman lines (resonance effect). In such a resonance Raman spectroscopy only the oscillation bands of the molecule part involved in the electronic transition are amplified.

Short excitation wavelengths in the blue/green have the advantage of an intensity of the Raman-scattered light increasing proportionally to $1/\lambda^4$, but can, in some cases, also efficiently excite fluorescences which then as an intensive background disturb the selective detection of the Raman signals. Hence, the environment of the Raman feature (substrate, printing inks, etc.) also plays a role when selecting the excitation wavelength. Preferably, wavelengths in the proximity of 1064 nm, 980 nm, 808 nm, 785 nm, 760 nm 670 nm, 630 nm, 532 nm, 445 nm, 405 nm or 380 nm are selected.

As an alternative to the use of a semiconductor laser there can also be employed an external, fiber-coupled laser, which at the position of the laser diode instead of it is coupled into the sensor via a fiber coupler. While this increases the volume of the assemblies, there also arise advantages with respect to laser power, beam quality, wavelength choice or frequency stability.

The laser can either be operated in pulsed fashion or continuously (cw), in the interests of a stable (i.e. chirp-free) excitation wavelength cw-mode is preferred, however.

The light of the excitation laser 101 is astigmatism-corrected with out-coupling optics, where applicable, and imaged with one or several lenses 102 as well as additional apertures, where applicable, into a parallel beam bundle. This is coupled into the main beam path 120 via a beam splitter 104 and is focused onto the bank note 150 to be checked with a lens system 103. These apertures are preferably designed to be absorbent in order to avoid uncontrolled scattered light or to minimize its intensity. In a preferred embodiment, the lens system 103 consists of one single lens.

The laser power on the bank note lies in the region of 1 mW to 10 W, preferably 10 mW to 1 W.

In a preferred embodiment, the focus spot has an extent of less than 5 mm, about 4 mm×2 mm, or 2 mm×0.5 mm, or 1 mm×0.3 mm. Here, the longer axis of the focus spot is oriented preferably perpendicular to the moving direction of the bank note which allows a higher spatial resolution in the moving direction. The size of the focus spot is geared preferably to the dimensions of an entrance slit, or slightly over-irradiates this by for example 20%. With such a design the dependence of the measured signal on the exact distance of the bank note relative to the Raman sensor 12 is advantageously reduced.

The power density in the focus region is between 0.1 $W/cm^2$ to 10 $kW/cm^2$, preferably between 5 $W/cm^2$ to 2 $kW/cm^2$. Here, the upper bound of the reasonably employable power density is given, among other things, by the damage thresholds of the bank notes to be checked, i.e. of the substrate, of the printing inks or of the feature substances. These damage thresholds may strongly depend on the wavelength.

Figure 3A:
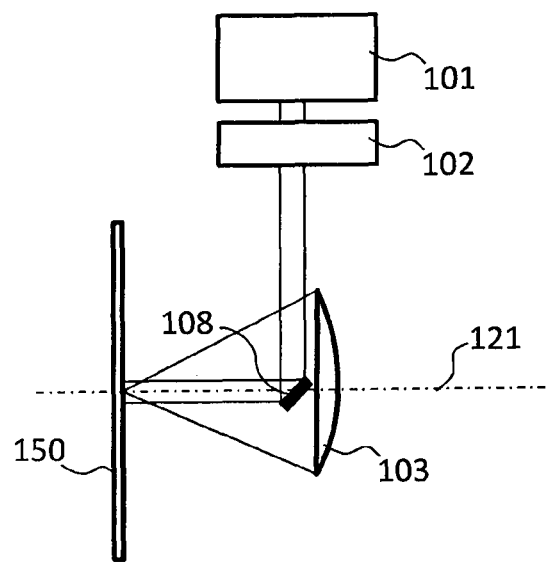

In another embodiment, the coupling in of the excitation radiation is not effected via a dichroic beam splitter, but via a conventional mirror. Here, the beam path of the excitation light and that of the light scattered at the bank note is decoupled via the mirror geometry. As schematically depicted in FIG. 3A, the in-coupling mirror 108 is positioned behind the lens system 103 and much smaller than the lens diameter. This achieves that only little of the scattered light gets lost by reflecting it out. The separation between Raman- and Rayleigh-scattered light here takes place with the filter 105 mandatory here, which can be configured as an edge filter or as a notch filter. As the excitation light is directed directly onto the bank note as a parallel beam bundle without lens, problems possibly occurring upon excitation because of variations in the focal position are avoided. The further beam path for collecting, spectrally decomposing and detecting the scattered light is effected analogously to the description of FIG. 2.

Alternatively, the coupling in of the excitation light via a small mirror can also be effected before the lens system 103, which in turn results in a focusing of the excitation light.

Figure 3B:
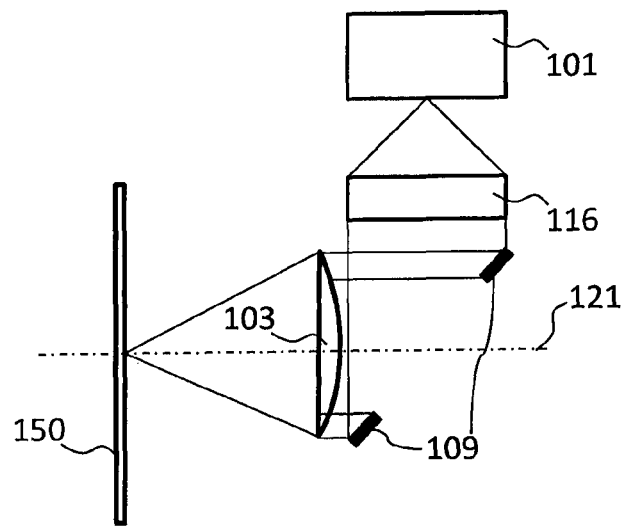

In another embodiment, the illumination with the excitation light is effected in an annular geometry. This is schematically illustrated in FIG. 3B. Here, by beam-forming laser optics 116 a toroidal or annular beam cross section is generated which is then focused via the lens system 103 onto the bank note by an elliptical mirror ring 109. Illumination geometries analogous to these embodiments can be also generated with fiber-coupled laser sources if the fiber couplers are positioned suitably. In a further instance, in the various mentioned embodiments of the illumination, the light of a second excitation laser with a different wavelength can be coupled in via suitably designed optics at component 102. The further beam path for collecting, spectrally decomposing and detecting the scattered light is effected analogously to the description of FIG. 2.

At the bank note 150 the excitation light is Rayleigh-scattered and Raman-scattered. Here, the intensity of the back-scattered light is clearly dominated by the Rayleigh-scattered portion. Both scattered light portions are directed by the lens system 103 as a parallel beam onto the beam splitter 104.

The beam splitter 104 as a dichroic beam splitter in a preferred embodiment is coated with a multilayer reflection filter which at the employed angle of attack, e.g. near 45°, acts as an edge filter. At the selected angle of incidence there is a high reflection degree, e.g. preferably greater than 90%, or more preferably greater than 95%, or particularly preferably greater than 99%, or >99.9%, for the excitation wavelength, while for the longer-wave, Stokes-shifted Raman light there is a substantially higher transmission portion. The transmission for Raman light Stokes-shifted by more than 300 $cm^{-1}$ is more than 70%, preferably 80%, particularly preferably 90%. In this form, the beam splitter 104, besides the geometrical coupling in of the light beam, at the same time advantageously contributes to the suppression of the excitation light in the detector.

In a preferred embodiment, the parallel beam with Raman light and a clearly reduced portion of Rayleigh light is imaged via one or several further optional filters 105 with a further lens 106 via a deflecting mirror 107 onto an entrance slit module 111.

In one embodiment, the one or more further filter(s) 105 act(s) as (an) absorption filter(s). This avoids the danger that the combined filter effect of the two interference filters 104, 105 could be reduced, compared to that of the individual filters, by interference effects due to multiple reflections. In another embodiment, the one or more further filter(s) 105 act(s) as (an) interference filter(s), in particular as an edge filter and serves for filtering the Rayleigh-scattered excitation light only insufficiently blocked by the inclined beam splitter or filter 104. In this context, also one or several polarization filters may be additionally introduced into the beam path to compensate the, in some cases, rather strong polarization dependence of the inclined beam splitter 104. For this purpose, in one embodiment, a linear polarization filter can be attached between lens 103 and bank note 150, which not only passes the linearly polarized laser light of the excitation radiation but also blocks the depolarized portion of the scattered light. Alternatively, the polarization filter can be positioned together with the filter 105, which also reduces at the laser wavelength the light possibly insufficiently filtered by the beam splitter.

In another embodiment, the deflecting mirror 107 is omitted and the light is imaged directly onto the entrance slit module 111 of the spectrometer 110 disposed in the main beam path 120 and now rotated by 90°.

In a further embodiment, the deflecting mirror 107 is simultaneously used as a remission monitor. If the excitation light is in the sensitivity region of silicon, i.e. in a wavelength region of approx. 350-1050 nm, depending on the silicon substrate, a silicon photodiode can be provided with suitable dielectric layers which reflect the Raman radiation to be detected but transmit the excitation light. With such a mirror/beam splitter the separation of the excitation light from the light to be detected can be improved (depending on the quality of the layer) and, in addition, the excitation light can be quantitatively captured. Hence, this beam splitter has also the function of a remission channel which proves the excitation light remitted by the BN. Such a construction also has the further great advantage that the excitation light disturbing in the spectrometer or detector is absorbed and thus not further mirrored in the sensor.

In other embodiments there is explicitly provided a particular detector for recording the intensity of the remitted, i.e. Rayleigh-scattered light.

In the spectrometer 110 the light of the entrance slit of the entrance slit module 111 is imaged by a lens system 112 onto a reflection diffraction grating 113, spectrally decomposed there, and after a new focusing by the lens system 112 imaged onto a detector 115. The lens system 112 here may consist either of a single aspherical or spherical lens, or comprise several lenses for correcting different imaging defects.

In an alternative embodiment, the combination of a planar grating 113 and lens system 112 can be replaced by an imaging concave grating which assumes both functions.

In case that the suppression of the excitation light by the filters 104 or 105 has not been effected completely and that this has only be distinctly weakened, this will also reach into the spectrometer 110. There, this light must also be handled very carefully, so that it will not impair the measurement as a scatter radiation. On the one hand, all orders (0th, −1st, −2nd, 2nd, . . . ) are absorbed in targeted fashion by beam traps, black walls, etc. In a preferred embodiment, the excitation light which is diffracted in the first (or analogously minus first) order is again directly imaged onto the slit. Thus, this light is mirrored out of the spectrometer 110 and can therefore no longer be disturbing in the spectrometer 110. Still, it should be attempted to absorb also this light within the Raman sensor 12 in targeted fashion. Due to the spectral proximity of the Stokes-shifted Raman light to the excitation light the detector 115 which is to prove the Raman light must be very near the entrance slit. This has the advantage that imaging defects are minimized and thus the construction can be very compact. But it is to be considered here that upon imaging the excitation light there also have to be taken into account imaging defects. Even when a foot of merely 0.1% would be observed, this could lead to a failure in the pixels of the detector 115 which are located directly beside the entrance slit.

Here, in the spectrometer 110, by accordingly positioned light-absorbent walls 114 there can be absorbed disturbing scattered light, and hence the background of the measurement can be reduced.

Alternatively, the excitation light can also be directed in targeted fashion into a beam trap within or outside the spectrometer 110, in which the light, of course, can also be proven. This can also be effected with spectral resolution. In a beam trap, of course, also absorption filters can be used.

The sufficiently weakened excitation light could also be detected with the detector 115. This has the advantage that the spectral distance to the lines to be detected can be directly measured and possibly occurring wavelength shifts can be corrected by an evaluation device 130. In a further embodiment, a coated absorption filter is attached to the detector 115, which again damps the excitation radiation to be detected.

The detector 115 preferably has a detector line of several photo-sensitive pixels, i.e. image points, arranged in series and is designed for the good spatial resolution of the Raman sensor 12 of the invention of less than 2 mm. As transport speeds of up to 12 m/s may occur for the value documents, in the case of a spatial resolution of 2 mm there is available, in the worst case, only a time of approx. 160 μs for the measurement of the total spectrum. Even with a reduced spatial resolution of 5 mm, only a maximum of 410 μs is available for the measurement of the spectrum. The detector 115 is accordingly designed for a readout time of less than 500 μs, preferably less than 100 μs. As weak signals are to be recorded with short integration times, the etendue of the system was optimized. For this, the cross-sectional area, i.e. the entrance slit has been selected relatively large. This has direct effects on the detector or on the scanned area on the bank note.

In a preferred first implementation, an especially sensitive and light-intense Raman sensor 12 with less than 100 spectral channels is employed.

Here a relatively large entrance slit with dimensions of, for example, 2×0.5 mm$^2$ is employed. The slit width is selected from the region of 0.2 mm to 1 mm, the slit length is 1.5 to 10 times larger than that. The aspect ratio of the entrance slit clearly deviating from 1 contributes to the fact that a large amount of light is collected on the pixels of the detector 115 without the spectral resolution being reduced too strongly here, because the width of the pixels in the dispersion direction can be kept small here.

The slit dimensions also directly define approximately the size of each individual pixel in the light-optimized system. In order for the restrictions through the expediently available overall space of the spectrometer 110 as well as the occurring imaging defects to be taken into account, with a slit size in the order of magnitude of 1 mm, the number of the pixels of the detector 115 will be limited to less than 100. In a particularly preferred embodiment, 32 spectral channels and thus 32 pixels for the detector 115 are selected.

The detector 115 comprises a number of pixels which corresponds to the number of spectral channels, the pixels having a relatively large pixel area and, compared to standard detectors, a portion of non-photosensitive regions between the pixels being diminished. While standard CCD lines have pixel dimensions of e.g. 15 μm or 30 μm, here the dimensions are in the mm region. This has the advantage that a clearly larger signal/noise ratio is achieved than with conventional CCD detector lines.

Preferably, the detector lines in this embodiment are constructed such that they merely have between 10 and 100, particularly preferably between 15 and 50 individual pixels in or on a substrate. The individual pixels may have dimensions of at least 0.5 mm×0.75 mm, preferably of 0.5 mm×1 mm, particularly preferably of 0.7 mm×2 mm. Preferably, the aspect ratio of the pixel dimensions is adjusted to the aspect ratio of greater than 1.5 of the entrance slit. The dimensions of the individual pixels may be different, e.g. in some positions or spectral regions twice or three times larger than in other positions. This permits the monitoring of particular spectral regions with different spectral resolution and may reduce the production costs of the sensor.

Advantageously, also the size and form of the illumination spot is adjusted to the size and form of the entrance slit, in order to lose as little as possible of the generated Raman light through the imaging of the luminous spot onto the entrance slit.

Depending on the wavelength region to be captured spectrally, in the mentioned cases the pixels of the detector 115 may consist of different materials. For Raman measurements in the ultraviolet or visible spectral region, detectors made of silicon which are sensitive to wavelengths below approx. 1100 nm are particularly suitable and for measurements in the infrared spectral region those made of InGaAs which are sensitive to wavelengths above 900 nm. Preferably, such an InGaAs detector line is applied directly onto a silicon substrate which particularly preferably has an amplifier stage produced in silicon technology to amplify the analogous signals of the pixels of the InGaAs detector line. By this there is likewise given also a particularly compact construction with short signal paths and increased signal/noise ratio.

Figure 4:
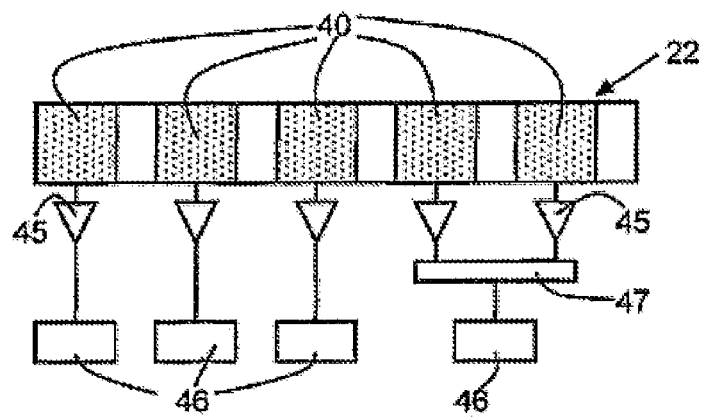

A readout of the individual pixels of the detector 115 can here be effected serially e.g. with the help of a shift register. Preferably, there is effected a parallel readout of individual pixels and/or pixel groups, however. According to the example of FIG. 4, the three left pixels 40 are respectively read out individually, by the measurement signals of these pixels 40 being amplified with the help of respectively one amplifier stage 45, which may be e.g. component of the silicon substrate, and fed respectively to an analog/digital converter 46. The two right pixels in the schematic representation of FIG. 4 again are first amplified by means of separate amplifier stages 45, then are fed to a joint multiplex unit 47 which, where applicable, may also comprise a sample & hold circuit, and then to a joint analog/digital converter 46 connected with the multiplex unit 47. The parallel readout of several pixels 40 or pixel groups made possible thereby makes possible short integration times and a synchronized measurement of the bank note. This measure also contributes to an increase of the signal/noise ratio.

In a second implementation, a Raman sensor 12 with a relatively high spectral resolution is employed which has a sensitivity slightly reduced compared to the first embodiment.

Here, an entrance slit with dimensions in the region of 25 μm×250 μm to 100 μm×1 mm is employed. The aspect ratio of the entrance slit clearly deviating from 1 again contributes to the fact that a large amount of light is collected on the pixels of the detector 115 without the spectral resolution being strongly reduced here, because the width of the pixels in the dispersion direction can be kept small. Preferably, a slit width is selected, which is 2 to 5 times the width of the pixel width on the detector 115.

As a detector 115 there is employed a fast readable CCD camera with synchronous integration time, preferably a CCD line-scan camera, in order to avoid the phenomenon of "image smearing" caused by moved objects. This would lead to a spatial/spectral smearing of the intensity values in the Raman sensor 12.

Preferably, for this there is selected a so-called interline or frame transfer architecture in which the charges collected by the individual pixels or photodiodes are shifted very fast into an optically densely darkened region of storage pixels, in which they can then be read out serially via a conventional shift register without distortion of the spectral information by further accumulation in the pixels read out later. In another embodiment, there is employed a CCD chip with high reading rate (higher than 30 MHz) and electronic shutter function which prevents an influencing of the accumulated charges during the readout.

In special embodiments, so-called TDI (time domain integration) CCD line sensors are used, in which a suitable line-by-line shift of the charge packets on the CCD detector chip synchronous to the movement of the imaging of the focus point on the moved bank note achieves a multi-step accumulation of the charges and thus amplification over several (e.g. 4 or 16) line cycles. This avoids that the detected signal is smeared over its structures, such as visible printing etc., by the motion of the imaged object. This is decisive in particular upon the detection of spatially structured codings, such as bar codes.

In a further embodiment, a fast readable CMOS camera with active pixel control and synchronous readout is employed. Here, too, a line sensor with high reading rate is preferably employed.

As an alternative to the line-scan camera, a camera with 2D array can also be employed, provided that the readout of the individual lines (i.e. spectra) is effected synchronously and sufficiently fast. This then allows an averaging over the various lines for improving the signal/noise ratio or, alternatively, a direct spatial resolution perpendicular to the moving direction.

The Raman sensor 12 in one embodiment is designed to record Raman light with a Stokes shift of 100 cm$^{-1}$ to 4000 cm$^{-1}$. In a further embodiment, the Raman sensor 12 is designed to record Raman light with a Stokes shift of 1000 cm$^{-1}$ to 3600 cm$^{-1}$ with a slightly higher spectral resolution. In this case, the larger spectral distance to the laser line simplifies the suppression of the excitation light. In a further embodiment, the Raman sensor 12 is designed to record Raman light with a Stokes shift of 1800 cm$^{-1}$ to 2600 cm$^{-1}$ with a particularly high spectral resolution, in particular better than 35 cm$^{-1}$, preferably better than 25 cm$^{-1}$.

In special embodiments, advantageously, the entrance slit module 111 of the spectrometer may fulfil several functions in combined fashion. On the one hand, it defines the entrance slit by its geometrical dimensions, on the other hand, a further filter function may be integrated therein and/or a measurement of the wavelength or power of the excitation laser may be performed.

Figure 5A:
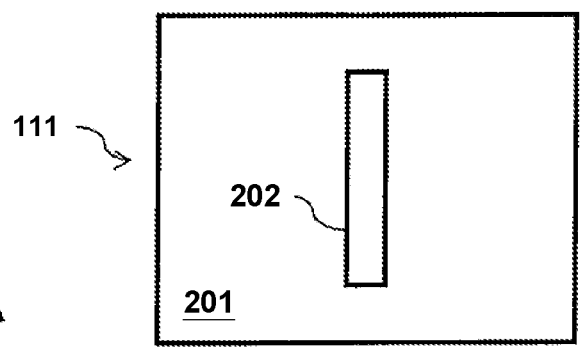
Figure 5B:
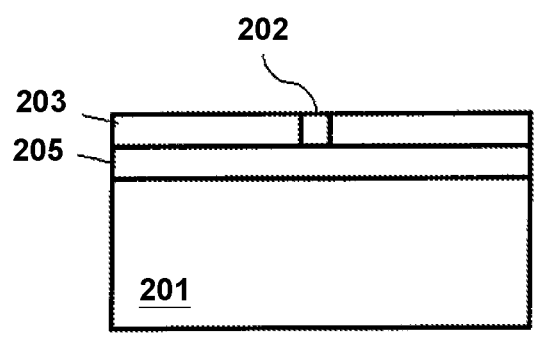

In FIG. 5A there is schematically shown a top view and in FIG. 5B a cross-sectional view of an embodiment of the entrance slit module 111 with combined filter effect. This comprises a carrier substrate 201 transparent to the Raman light at least in some spectral regions, which is coated with a layer 203 opaque to the excitation light and to the Raman light. This layer preferably acts absorbent to the spectral regions of the excitation light and Raman light to prevent uncontrolled reflections in the sensor. The opaque layer may here comprise absorbent inks, metals, such as Cr, Ti, Ni, etc. as well as their oxides, sulphides, and/or broadband absorbers, such as carbon (carbon black). Into the layer 203 there is structured an opening which acts as an entrance slit 202. This can be effected either additive by printing or vaporizing, e.g. in shadow mask technology, or subtractive by applying a closed layer which in a second step is structured, masked and etched free.

In one embodiment, the semitransparent substrate 201 itself acts as an absorption filter for the excitation radiation. This can be effected, for example, by employing a silicon crystal as a substrate for the entrance slit module 111 in combination with an InGaAs-based detector 115. This allows the excitation radiation smaller 1100 nm to be selectively absorbed, while the Raman radiation in the infrared spectral region is transmitted and can be detected by the detector 115. In order to improve the filter effect and/or be able to set spectral curves for the filter effect in targeted fashion, one or several further filter layers 205 may optionally be applied. These may comprise dielectrics and also absorbers.

In another embodiment, in the entrance slit module 111, beside the geometrical definition of the entrance slit, there is performed a measurement of the wavelength and/or of the power of the excitation laser 101. This information is advantageously employed for controlling or stabilizing the excitation laser. This can be used independently or in combination with the described embodiments with filter effect.

Figure 6A:
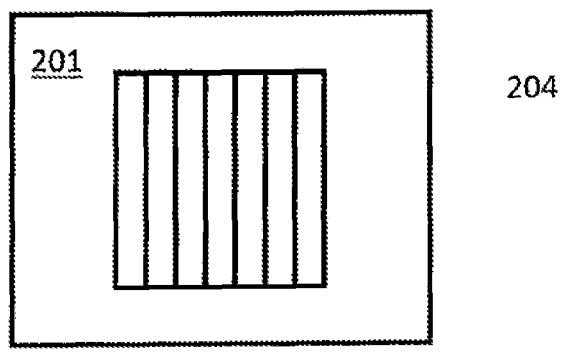
FIG. 6A illustrates schematically in a top view the back side of an embodiment of the entrance slit module with integrated wavelengths and/or intensity monitor of the Rayleigh-scattered excitation radiation, FIG. 6B, C illustrate schematically in a cross-sectional view various embodiments of the entrance slit module with integrated wavelengths and/or intensity monitor of the Rayleigh-scattered excitation radiation, and FIG. 7A-D background-corrected intensity data of different feature substances in 32 spectral channels.

Here, as illustrated in FIG. 6A, on the side facing away from the entrance slit, on or in the substrate there is formed an arrangement of photodiodes 204. In the case that the substrate 201 consists of silicon or other suitable semiconductors, these can be directly formed in the substrate 201 with the corresponding methods of semiconductor manufacturing. In other cases, such as in the case of a glass substrate, the photodiodes can either be formed on the substrate in thin film technology or alternatively can be mounted there. The wavelength measurement of the excitation radiation here is achieved by designing the spectrometer or its grating such that the first diffraction order of the excitation light—at least at its nominal wavelength—is thrown back from the grating again back in itself onto the entrance slit. If now the wavelength of the excitation radiation deviates from the nominal value due to drifts or variations, the first diffraction order is no longer thrown back exactly onto the entrance slit but in a slightly deviating direction which is detected accordingly by the adjacently attached photodiodes.

Figure 6B:
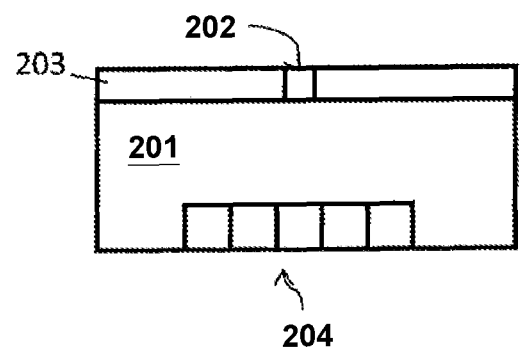

In FIG. 6B, the situation is illustrated in an embodiment example, in which the photodiodes are positioned in the substrate 201 and this acts—for example formed from Si—at the same time as a filter for short-wave excitation radiation. The light incident through the slit 202 in the opaque layer 203 is filtered by the substrate 201 and the intensity of the Rayleigh-scattered (and filtered) from the bank note is determined with the central pixel of the photodiode arrangement 204. With an excitation radiation wavelength deviating from the nominal value more light falls onto the adjacent pixels of the photodiode arrangement 204, which can be utilized for the quantitative determination of the excitation wavelength.

Such a slit module is used preferably in combination with an InGaAs detector.

Figure 6C:
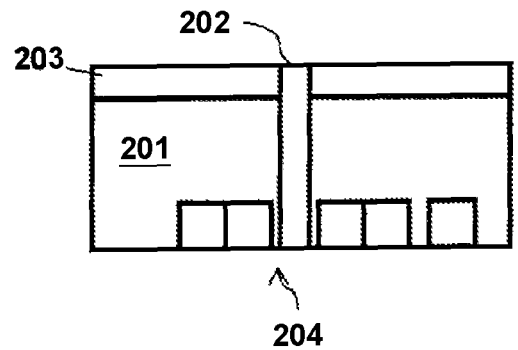

A further embodiment is schematically illustrated in the cross section in FIG. 6C. Here, a physical slit 202 is configured through both the opaque layer 203 and the complete substrate 201, so that no filtering or absorption of the incident light takes place in the input slit module 111. The physical slit 202 can be configured, for example, by etching a corresponding trench through the substrate 201, which may consist e.g. of silicon. This embodiment is preferably employed when the wavelength of the excitation radiation is to be monitored and when both excitation and Raman radiation are in the absorption region of the (silicon) substrate 201. Alternatively, also separate detector elements may be suitably positioned in the spectrometer 110—independent of the design of the diffraction grating 113—for monitoring the excitation radiation.

Starting out from the measured intensity values of the individual spectral channels of the Raman spectrum linearly scaled in wavelengths (nm), a processing and evaluation of the measurement data is effected in the evaluation unit 130 of the Raman sensor 12. For this, first a possibly present background portion is determined and subtracted from the measured intensity values in order to obtain background-corrected intensity values.

In one embodiment, for this, the moving minimum is calculated over n nodes of the measured intensity values. The number n of nodes is geared to the total number of spectral channels and the spectral resolution of the measuring region and, advantageously, is selected such that n exceeds the number of measuring points which resolve one individual peak. If the typical (e.g. most intensive) Raman peaks consist of, for example, three measuring points, then preferably at least five or at least seven channels are employed for the calculation of the moving minimum as an estimated value for the background.

In a more general embodiment, a moving percentile, e.g. the lowest 10%, lowest 30% or the median with 50% is selected to determine the course of the background. This has the advantage that individual outliers caused, e.g. by noise do not carry an unduly high weight.

In a further embodiment, nodes to be employed for the calculation of the background are explicitly specified. This offers the advantage that there can be selected in targeted fashion spectral regions from which in the case of an authentic (and freshly printed) bank note no significant Raman signal is to be expected. These are selected preferably in the region of 1900-2500 $cm^{-1}$, because in this spectral region none of the feature substances preferably employed for marking has Raman lines. This enables a particularly reliable determination of the background.

After the spectral channels with their measured intensity values to be used for the background subtraction were selected, these are interpolated by a polynomial adaption and the background-corrected measurement data are formed by subtraction of the interpolated values from the measured intensity values. In the easiest case a linear adaption is selected for the polynominal adaption, in other cases there can be selected a polynom of higher degrees, cubic splines, etc.

In the next, optional, step the background-corrected measurement values are normalized. For this, in one embodiment, the maximum of the background-corrected measurement values is determined and the background-corrected measurement data are divided by this maximum value, so that normalized background-corrected measured values lying in the interval [0, 1] are obtained.

Subsequently, in one embodiment, the evaluation of the measured intensity values is effected by the peak positions of the Raman spectrum being determined. For this, a list of the channel indexes of the local maxima is created in the discrete measurement value array of the spectral channels. Alternatively, a list of interpolated peak positions is created. For this, the apexes of parabolas are employed, which are respectively defined by three points whose central point employed for the adaption respectively corresponds to a local maximum of the measurement values. With this method there can be determined even more precise spectral positions—also more precise than the nominal spectral channel spacing. This method delivers results identical to the likewise possible method of determining the interpolated zero values of the derivative.

After the peak positions of the Raman spectrum were determined, there is optionally effected a selection of the peaks to be employed for the further authenticity recognition. Either only peaks with a particular minimum intensity may be used. Alternatively, only peaks with a maximum full width at half maximum or with a full width at half maximum in a specified region between a lower and an upper threshold may be used for the further evaluation. Alternatively, only the k highest peaks may be employed for the further evaluation or for the authenticity recognition.

In the further course of the evaluation there are different possibilities: either a direct verification of the measured Raman spectrum is effected, i.e. a comparison with a reference spectrum of an authentic bank note or a comparison with a library of various authentic reference spectra, or there is first carried out a classification with a subsequent verification. The first possibility is particularly advantageous, when the Raman sensor is adapted exclusively for the authenticity recognition of one single denomination, i.e. if only one single, firmly specified authenticity feature must be recognized. The latter method is expedient in particular when several different currencies and different denominations are to be recognized with the help of the Raman spectrum (i.e. comparison with an entire library of Raman fingerprints), because a classification algorithm is often faster than a verification algorithm.

The numerical classification of the (normalized) background-corrected measurement value in one embodiment is effected via a statistical classification, e.g. by estimating the scattering point clouds of the individual class members by normal distributions. Based on these, the most likely class affiliation can be ascertained which is then verified with a verification algorithm. Alternatively, a next-neighbour classificator, support vector machines, a polynom classificator, a neural network, or a Fisher linear discriminant are used for classification. There may likewise be selected the class which shows the greatest similarity with respect to the correlation between the measured spectrum and the reference spectrum. All classification methods can not only be applied to the original curves (i.e. the normalized background-corrected measurement values), but also to their derivatives.

In general, the verification is finally effected by the calculation of a similarity measure between the measured Raman spectrum and the reference spectrum. The similarity measure may be a Euclidean distance, a squared Euclidean distance, normalized squared Euclidean distance, Manhattan distance, checkerboard distance, Bray-Curtis distance, Canberra distance, cosine distance, or a correlation distance.

In another embodiment, the particular spectral positions of the essential peaks may be directly compared with a table of the reference spectrum, i.e. it is checked whether the measured Raman spectrum at exactly specified places— within a tolerance in the form of a real number in the case of interpolated peak positions or of a discrete tolerance in the case of a channel index—matches the reference spectrum. In one embodiment, in doing so, merely the spectral position of the peaks is compared, in other embodiments, additionally the relative or absolute intensities.

In a preferred embodiment, a uniform correction of a spectral channel shift can be effected, as it may be caused, for example, by a fluctuating wavelength of the excitation laser. The degree of the spectral shift which is required for this correction can be determined, for example, with the help of the measured spectral position of a, e.g. the most intensive peak and the comparison with the target value. Expediently, the permissible maximum shift is still further restricted by a threshold value in order to not unnecessarily weaken the authenticity recognition.

Alternatively, the verification can be effected by checking whether the measured Raman spectrum has peaks in at least individual specified places. For this, there are advantageously employed the most intensive peaks of the Raman spectrum. Here, likewise, again a real or discrete tolerance may be allowed in order to recognize a match.

In a further embodiment it is checked, whether the correlation $<x, y>/(|x||y|)$ between the measured (background-corrected and perhaps normalized) Raman spectrum and a reference spectrum exceeds a certain threshold. This is e.g. the case, when the correlation is greater 0.7, preferably greater 0.8, further preferably greater 0.95. Here, $<x, y>$ designates the scalar product between the two spectra x or y regarded as vectors and | | the absolute value of the respective vector.

Alternatively, the derivative of the Raman spectrum and of the reference spectrum is determined and it is checked whether the correlation between these exceeds a predefined threshold.

Preferably, the correlation is calculated several times, the reference curve being spectrally shifted step by step in a small region. In so doing, one obtains a correlation curve. With the maximum of the correlation curve there is simultaneously determined the optimum channel correction for the correction of any laser drift of the excitation laser 101 and with a sufficient numerical value of the correlation coefficient there is verified the class affiliation. Here, too, the permissible maximum shift is expediently restricted by a threshold value in order to not unnecessarily weaken the authenticity recognition.

In a particularly preferable variant, the wavelength of the excitation laser 101 can be measured directly in the Raman sensor 12 and this measurement value can be employed for correcting the spectral channels. This is of advantage in particular with a dense Raman spectrum with many peaks (in the worst case also approximately equally high peaks), because otherwise it cannot be determined reliably which peak was shifted in which direction.

Alternatively it is also possible to carry out these comparisons or the calculation of the similarity measure employed for the verification with the Fourier transform of the normalized background-corrected measurement values in comparison to the Fourier transform of the reference spectrum.

As the excitation laser 101 of the Raman sensor 12 operates, in the interest of an optimum signal intensity, at high powers slightly below the destruction threshold, in a preferred embodiment, additional measures are taken to reliably prevent a damage of the bank notes to be checked.

In a first step it is prevented that in the case of a transport fault or when a bank note jam occurs a bank note 150 remains permanently in the focus spot of the excitation laser 101 and is improperly strongly heated up there. For this, there is advantageously employed the signal of the excitation light remitted or back-scattered from the bank note 150, obtained in the Raman sensor 12, which is modulated according to the printed image of the bank note 150. If now the signal of the remitted light remains constant over several measurement cycles, in particular at a rather low level, a bank note jam will be recognized and the power of the excitation laser 101 is reduced or switched off. In a further embodiment, an additional remission sensor or light scanner is provided, which assumes this task. For this, the light remitted (back-scattered and emitted) from the bank note under illumination is measured. Preferably, the excitation light exits from the Raman sensor 12 only when a bank note 150 is positioned in front of the Raman sensor 12 (e.g. remission greater 0 or greater 0.05) and when this does not rest, i.e. the remission signal is subjected to temporal fluctuations.

In a further embodiment, the power of the excitation laser 101 is dynamically adjusted to the current absorption ratios on the bank note 150. Here, the power of the excitation laser 101 varies between at least two power stages, the nominal (high) power and at least one reduced power stage. If the measured remission undershoots a particular value, e.g. greater 0.3 or greater 0.15, the power of the excitation laser 101 is reduced to the lower power stage, with which a damage of the bank note 150 is excluded. As the excitation laser 101 is not switched off completely, the determination of the remission is possible also at the next measuring point. In this way, a change back again to the high excitation power can be performed, when e.g. one or several measuring points of the remission again are above a switching-on-threshold value.

In a further, preferred embodiment, the Raman sensor 12 has an additional measurement point for the remission measurement, which in the moving direction of the bank note is positioned in front of the measurement point of the Raman sensor 12. The remission of the bank note 150 is thus monitored before the Raman measurement and for every measurement place on the bank note 150 it can be determined in advance which excitation power is to used there, or whether there is to be effected a Raman measurement at all.

This remission measurement is preferably effected with an illumination wavelength near the laser wavelength employed for the Raman measurement to obtain representative remission or absorption values. This enables a signal-optimized Raman measurement and at the same time it is ensured that the bank note 150 cannot be damaged.

Typical Raman molecule vibrations occur in the region of 200 to 4000 wave numbers ($cm^{-1}$). This region can be roughly divided into subregions for vibrations of specific groups.

For forming a Raman feature, the marker molecules are brought into a suitable particle form by grinding or, where applicable, by adsorption or bonding to other substrate or matrix substances, and are encapsulated, where applicable, to protect them from environmental impacts.

For forming an SERS feature, the marker molecules are brought into close (e.g. direct) contact with a metallic nanoparticle ("antenna") which via surface-plasmonic effects leads to a drastic amplification of Raman signals of the marker molecule. The combination of marker molecules and antenna particle is encapsulated, where applicable, to protect them from environmental impacts. For a more detailed description of production methods of SERS features reference is made to e.g. EP 0806460 B1 or WO 2014/022330 A2.

In a preferred embodiment, organic molecules are used as marker molecules. These have, among other things, C—H— and C—C-bonds, which form characteristic signals. For example, the C—H vibrations of saturated carbon groups cause, e.g. with molecules having alkyl chains, strong signals in the region of 2700-3200 $cm^{-1}$.

A strong signal in the region of 2000-2200 $cm^{-1}$ is typical for C—C or C—N triple bonds, e.g. with molecules having nitrile groups. Strong signals of unsaturated C—H vibrations occur typically in the region of 1300-1800 $cm^{-1}$, e.g. with molecules having allyl groups. Strong signals from vibrations where two or more connected carbon atoms are involved, such as e.g. so-called lattice vibrations, may occur in the region of 1300-200 $cm^{-1}$. In particular aromatic unsubstituted phenyl groups have a very strong, characteristic signal at 990-1100 $cm^{-1}$.

In a usual (forensic) analysis of a high-resolution Raman spectrum, by evaluating small differences in the band positions or the occurrence and the ratios of several small bands in these regions there can be drawn inferences about the identity of the molecule or the molecule can be identified.

Upon analysis of a high-speed measurement the exact molecule identification is no longer possible due to the clearly decreased spectral resolution. Here, instead rather qualitative properties of the employed marker molecules, such as the existence of a strong phenyl band in the region of 990-1100 nm, the existence of a C—C triple bond in the region of 2040-2080 $cm^{-1}$, or the existence of an extensive region of alkyl vibrations in the region of 2800-3000 $cm^{-1}$ are queried and integrally quantitatively accessed for authenticity recognition.

An especially good security recognition with strong discrimination against forgery substances is achieved with the Raman sensor according to the invention when this is adjusted with its properties to the employed feature substances and vice versa, when upon selection of the employed feature substances these are selected specifically in view of the proof with the Raman sensor.

For preparing a coding system for value documents, which coding system is suitable for the differentiation and identification with the sensor according to the invention, there are different preferred embodiments.

For this, the value documents are marked with feature substances or mixtures of feature substances which comprise marker molecules having strong Raman signals in one or several spectral regions respectively with a spectral distance of more than 50 $cm^{-1}$, preferably more than 100 $cm^{-1}$, particularly preferably more than 200 $cm^{-1}$. For this, marker molecules with one or several molecule structures with conjugated multiple bonds, differently substituted double bonds, a different number of double bonds, C—C triple bonds, unsubstituted phenyl groups, mercaptans, S—H bonds, P—H bonds or fluorine groups are employed.

In a first preferred embodiment, a coding is created by selecting a group of feature substances which all have strong signals in an individual region. The strong signals of the substances must significantly differ from each other here. For example, a series of molecules with differently substituted double bonds and/or different number of double bonds can be created. The spectral resolution in the selected region is then increased by doing without remaining spectral regions located farther away. By employing a grating dispersing stronger there can be achieved, while accepting a limited spectral region, a higher spectral resolution in the region that is especially well for reliably identifying the selected feature substances. This enables a reliable identification of the individual feature substances employed for the coding with the help of a Raman measurement at high speed.

In a further preferred embodiment several regions are measured. For this, the Raman sensor can be equipped with several gratings which allow a scanning of different spectral regions with high resolution (with limited number of the total channel number). Analogously, a grating with corresponding detector can be used for monitoring a wide spectral region with low spectral resolution e.g. as to the absence of corresponding Raman signals, while a second grating disperses with high resolution the spectral region characteristic for the employed feature substance to allow a reliable allocation or identification of the marker molecule here.

For preparing a coding system, feature substances or mixtures of feature substances having strong signals in several regions are selected. For distinguishing the individual feature substances, the strength or the presence/absence of signals of the individual regions is then used. For example, a coding could be made by considering the three regions of 2040-2080 $cm^{-1}$ (C—C triple bond), 990-1100 $cm^{-1}$ (unsubstituted phenyl groups) and 2800-3000 $cm^{-1}$ (alkyl chains). Here, even with the diminished spectral resolution of a high-speed measurement, a first coding substance (including a triple bond, an unsubstituted phenyl group, but no alkyl groups) can be distinguished from a second coding substance (including a triple bond, no phenyl groups, but alkyl groups) and a third coding substance (including no triple bond, an unsubstituted phenyl group as well as alkyl groups).

In a further preferred embodiment, a marker molecule with a triple bond is selected as a feature substance. Here, the spectral resolution is selected preferably so high that a C—C triple bond (typically at 2040-2065 $cm^{-1}$) can still be separated from a C—N triple bond (typically 2080-2105 cm–1).

Preferably, a correction of the background is carried out, e.g. to balance fluorescence interference effects, by supporting points in the region of 1900-2500 $cm^{-1}$, because here, except for the well defined individual signal peaks of the triple bonds, no further Raman disturbing signals occur. Occasional exceptions are e.g. the allenes and cyanates, which, however, are relatively exotic just as the molecules with triple bonds and hence do not occur in compounds usually present in or on bank notes.

In a further preferred embodiment, as feature substances there are selected compounds which have specific groups with spectral band positions which do not occur as substances typically contained in bank notes. These are, besides the already mentioned triple bonds, e.g. also conjugated multiple bonds, mercaptans and further S—H bonds with characteristic signals in the region of 2510-2540 cm$^{-1}$ as well as P—H bonds (signals in the region of 2090-2500 cm$^{-1}$) or fluoride compounds.

In a preferred embodiment, instead of purely organic matters there are used metalorganic matters or inorganic matters as feature substances, for example, in the form of metalorganic chelate complexes or pure metal complexes or salts or oxides. The Raman signatures of metalorganic complexes often differ strongly from the typical bank note background which promotes an undisturbed measurement. Also ceramic compounds show significant Raman bands which permit unambiguous allocations and clearly distinguish an inorganic feature substance from paper additives such as titanium dioxide or barium sulphate.

The Raman or SERS feature substances which are proven with the Raman sensor of the invention can be introduced into the volume of individual components of the value documents. The feature substances can be introduced into the substrate volume or into the polymer composition of security threads, transfer strips, mottled fibers or planchets upon the papermaking by metering them into the pulp. Additionally or alternatively, the feature substances can be mixed into a printing ink or coating composition and be applied onto the surface of the value document with conventional printing methods. In this case, spatial codings in the form of bar codes, 2D bar codes, signs, forms or symbols can be effected which can be proven with the spatially resolving sensor.

It is desirable to record the Raman spectra at as many positions per bank note as possible. This is effected at least along a track over the bank note with the help of which the position of introduced or applied SERS or Raman feature substances can be determined and checked. Likewise, this allows a (1D) bar code information to be read out by determination of the variation of the signal intensity depending on the position on the bank note.

In one embodiment, several parallel tracks, e.g. 2 tracks, 3 tracks, 4 tracks or more over the bank note are recorded.

In the simplest variant, for this all the optical components of the Raman sensor 12 are executed several times according to the number of tracks and are positioned according to the orientations of the tracks. This has the advantage that the optical beam positioning of every track is completely separated from the other tracks and no interaction such as e.g. crosstalk or incidence of scattered light is to be feared.

In a more cost-efficient embodiment individual components are used jointly by the different tracks. This is expedient e.g. for the diffraction grating 113 or the beam splitters 104, 107. Here, a uniform illumination for all the tracks can be employed, which then is focused either in the form of one single homogeneous line vertically to the transport direction of the bank note or, alternatively, is focused by focus lenses individual for every track in several circular or elliptical focus points. In both cases only one—where applicable more powerful—excitation laser 101 is required which assumes the excitation for several channels. The separation of the tracks in this embodiment is effected on the detection side in the first place, each track having its own detector system and the spectra of each track being recorded separately.

In a preferred embodiment, the Raman light emanating from the value document is scanned along several tracks, by it being coupled into respectively one light guide in the form of a flexible glass fiber or a rigid light guide at the height of each track position by a lens system 103 or 106. Now the light guides direct the Raman light of the different track positions together onto different, preferably adjacent height positions of the entrance slit of a spectrometer jointly employed for several tracks. This allows the Raman spectra of the different track positions being captured either with line detectors attached at different height positions, or alternatively with an individual, two-dimensionally resolving detector array. Here, the detection along the dispersion direction of the spectrometer is effected simultaneously, while reading out the direction vertically thereto may be effected with a time shift. With this design the construction volume of the sensor can be clearly reduced compared to a variant with several individual spectrometers.

In a further implementation variant, the recognition reliability upon the identification of the Raman or SERS feature is increased by the Raman spectrum being checked and proven at more than one excitation wavelength. This allows Raman peaks to be reliably separated from e.g. fluorescent peaks which do not spectrally shift with the excitation wavelength. For this, a second laser light source is provided in the sensor, this may be coupled into the beam path together with the first laser light source or may employ a separate optics system. The second excitation wavelength can be spectrally relatively far away from the first excitation wavelength, e.g. 532 nm and 785 nm, or alternatively spectrally relatively close to the first excitation wavelength at a distance of some nm, preferably of 1 nm to 50 nm, in particular 2-20 nm. The detection of the Raman responses at both excitation wavelengths is possible either sequentially or simultaneously. In particular with simultaneous detection the Raman spectra are complicated, because then all peaks appear twice or in a shifted manner which may render the analysis for a forgery attack more difficult.

In addition, there may possibly arise an overlapping of Stokes- and Anti-Stokes-shifted Raman lines in the measured spectral region which overlap or supplement each other at the spectral positions specified by the selected excitation wavelengths and thus generate a unique "fingerprint" dependent on the selected excitation wavelengths.

In particular, by employing 2 excitation wavelengths there can be evaluated a combination feature with luminescence and Raman signals and the respective contributions can be separated from each other, which represents a further increase of the forgery complexity compared with the measurement of such a combination feature with only one excitation wavelength.

In a preferred embodiment, there is effected a sequential illumination with excitation light of a slightly different wavelength or spectral distribution and detection of respectively one spectrum with the intensity distributions $I_1(\lambda)$ or $I_2(\lambda)$. For evaluation, the two obtained spectra can now be subtracted from each other and normalized, where applicable, with the spectral distance $\Delta\lambda$ of the excitation wavelengths. In this difference spectrum the background contribution of scattered light or fluorescence radiation is effectively eliminated, so that, for the authenticity evaluation, these can be advantageously compared either directly with analogously formed difference spectra of authentic bank notes or with the derivative dI/dλ, of the reference spectrum of authentic bank notes obtained at an excitation wavelength.

In a particularly preferred embodiment, an illumination is alternately effected with excitation light of a first, narrow-band laser source at a first wavelength and alternating thereto with two laser lines which are spectrally closely adjacent, preferably at a distance of 1-50 nm, in particular 2-20 nm to each other. Preferably, the two laser lines at the first wavelength and at a second wavelength are at a distance of 1-50 nm, in particular 2-20 nm from the first wavelength. Further preferably, the spectral distance of the double line is advantageously tuned to an integer multiple of the spectral distance of the channels of the detector. In this case, upon excitation with the double line, no partial overlaps occur between adjacent spectral channels, which avoids artifacts.

A suitable light source with selective single and double line emission can be realized, for example, by coupling in a first laser source and a second laser source in combined fashion. Both laser sources are preferably mono-mode lasers, e.g. DFB lasers, so that by driving one laser or both lasers the desired spectrum of excitation radiation can be easily controlled. Particularly preferably, the first and the second laser sources are coupled as oscillators into an optical power amplifier in a MOPA architecture (master oscillator power amplifier). This has the advantage that an identical coupling in of the excitation radiation onto the bank note to be checked is ensured, because in spite of different spectral distribution the starting point or the beam profile of the excitation radiation is always determined by the same construction element, namely the power amplifier.

With this illumination scheme of the excitation radiation, upon illumination with the double line there is obtained with the sensor a Raman spectrum with twice occurring Raman peaks and singly occurring fluorescence peaks, while upon illumination with the mono-chromatic excitation radiation each Raman peak occurs individually in overlap with a possible fluorescence background. If now, after normalization of both spectra, the spectrum obtained with mono-chromatic excitation radiation is subtracted from the spectrum obtained with the excitation radiation with the double line, not only the fluorescence background is deleted even in difficult or intensive cases, but at the same also the Raman double peaks are reduced to a simple Raman spectrum having only individually occurring peaks. For authenticity evaluation, this Raman spectrum can now be compared in an especially simple manner with reference spectra of authentic bank notes, without further unfolding being necessary.

The FIGS. 7A to 7D represent background-corrected measurement data of the Raman sensor 12 for four different feature substances in a division of the spectral channels scaled linearly in the wavelength. The excitation wavelength was 488 nm. The background portion of the intensity values in the spectral channels was determined by the moving minimum of respectively five spectral channels and was subtracted from the intensity values.

Figure 7A:
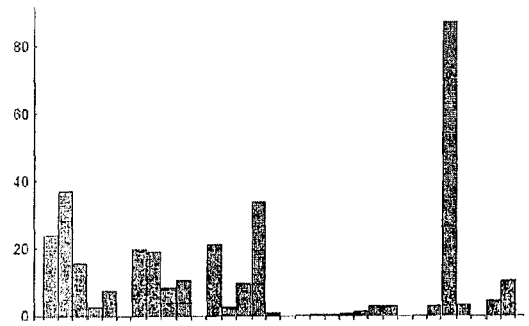
Figure 7B:
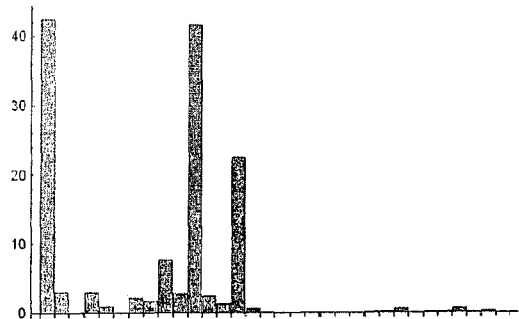
Figure 7C:
Figure 7D:
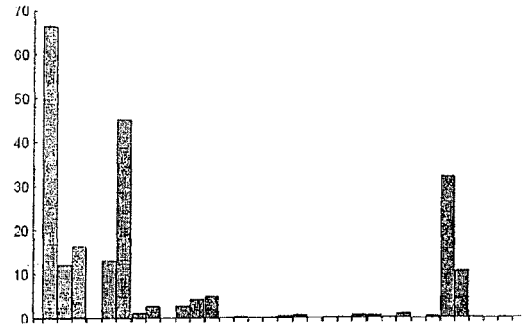

The four different feature substances are based on the four different marker molecules citric acid (FIG. 7A), nitrobiphenyl (FIG. 7B), diphenyloxadiazole (FIG. 7C), and tetrachlorobutane (FIG. 7D). One can recognize that the four different feature substances, in spite of the spectral resolution being reduced in comparison to a laboratory spectrometer, can be distinguished from each other or identified very well with the help of their respective spectral fingerprint with signal contributions in spectral regions quite far apart from each other.

The invention claimed is:

1. A sensor for the machine check of moved value documents having at least one Raman or SERS or SERRS security feature, wherein, for checking, the sensor is configured to illuminate the value document with excitation light from a laser source and to disperse a resulting Raman light of the security features in a spectrometer and to capture it with spectral resolution with a detector having several spectral channels;
   wherein the light from the same areal region of the value document collected in the spectral channels is captured synchronously by the detector and measurement signals corresponding to the spectral channels are formed: and
   wherein scattered excitation light emanating from the value document is coupled via a slit module into the spectrometer such that Rayleigh-scattered excitation light is re-imaged onto an entrance slit, wherein the slit module has an absorption element which absorbs the Rayleigh-scattered excitation light at least partly.

2. The sensor according to claim 1, wherein the synchronous capture of the spectral channels is effected within less than 500 µs.

3. The sensor according to claim 1, wherein the sensor has a spatial resolution in a moving direction of less than 12 mm.

4. The sensor according to claim 1 wherein the spectral channels are read out in parallel at the same time.

5. The sensor according to claim 1, wherein the sensor has less than 100 spectral channels.

6. The sensor according to claim 1, wherein the excitation light of an excitation laser directs via a beam splitter inclined toward a main beam path in the direction of the value document to be checked, wherein the beam splitter is configured as an edge filter for the selective reflection of the excitation light.

7. The sensor according to claim 1, wherein the scattered excitation light emanating from the value document is coupled via the slit module into the spectrometer, wherein the slit module has a detector element for monitoring power and/or wavelength of the Rayleigh-scattered excitation light.

8. The sensor according to claim 1, wherein a power of the excitation light is selected in dependence on a measured remission signal.

9. The sensor according to claim 1, wherein a power of the excitation light is reduced, when a measured remission is smaller than a threshold value or the measured remission does not change over several measurement cycles.

10. The sensor according to claim 1, wherein the sensor further has an evaluation unit which determines from the measurement signals corresponding to the spectral channels a background portion and subtracts this from the measurement signals to generate background-corrected measurement signals, wherein the background portion is determined with the help of a moving percentile from intensity values or with the help of the intensity values in predetermined spectral channels.

11. The sensor according to claim 1, wherein, for checking, the sensor is configured to further illuminate the value document with excitation light from a second laser source and to disperse resulting Raman light of the security features in the spectrometer and to capture it with spectral resolution with the detector having several spectral channels.

12. The sensor according to claim 1, wherein the sensor is configured to illuminate the value document with a laser line at a first wavelength and alternating thereto with two laser lines having a spectral distance of 1-50 nm.

13. The sensor according to claim 1, wherein the sensor is suitable for distinguishing and identifying a coding with feature substances, wherein the feature substances comprise marker molecules, wherein the marker molecules have strong Raman signals in one or several spectral regions with a respective spectral distance of more than 50 cm$^{-1}$.

14. A method for the machine check of value documents having at least one Raman or SERS or SERRS security feature by means of a sensor, wherein
    during the check, the value document is moved relative to the sensor at high speed,
    for checking, the value document is illuminated with excitation light from a laser source,
    resulting Raman light of the security features is dispersed in a spectrometer,
    is captured with spectral resolution with a detector having several spectral channels,
    measurement signals corresponding to the spectral channels are formed, wherein the light from the same areal region of the value document collected in the spectral channels is captured synchronously by the detector and spatially resolved measurement signals are formed by repeated measurement, and
    the scattered excitation light emanating from the value document is coupled via a slit module into the spectrometer such that Rayleigh-scattered excitation light is re-imaged onto the entrance slit, wherein the slit module has an absorption element which absorbs the Rayleigh-scattered excitation light at least partly.

15. The method according to claim 14, wherein in the measurement signals corresponding to the spectral channels a background portion is determined from intensity values with the help of a moving percentile, or determined with the help of the intensity values in predetermined spectral channels and interpolated by a polynomial and subtracted from the intensity values and hence background-corrected measurement values are calculated.

16. The method according to claim 15, wherein a numerical classification of the background-corrected measurement values is carried out.

17. The method according to claim 14, wherein an authenticity recognition of the value document is carried out by a verification algorithm which is based on the calculation of a similarity measure between a measured spectrum and a reference spectrum.

18. The method according to claim 17, wherein a spectral shift of intensity values within a predetermined region is corrected or is tolerated upon the authenticity recognition.

* * * * *